United States Patent [19]

Farge et al.

[11] 3,946,019
[45] Mar. 23, 1976

[54] 7H-INDOLIZINO [5,6,7-IJ]ISOQUINOLINE DERIVATIVES

[75] Inventors: Daniel Farge, Thiais; Yves le Goff, Breitgny-sur-Orge; Mayer Naoum Messer, Bievres; Gilbert Poiget, Thiais, all of France

[73] Assignee: Rhone-Poulenc, S.A., Paris, France

[22] Filed: July 25, 1974

[21] Appl. No.: 491,642

[30] Foreign Application Priority Data

July 27, 1973 France .............................. 73.27649
Nov. 22, 1973 France .............................. 73.41616
May 30, 1974 France .............................. 74.18808

[52] U.S. Cl. .... 260/287 P; 260/283 CN; 260/28.35; 260/286 R; 260/288 D; 260/288 CF; 260/289 C; 260/347.8; 424/258
[51] Int. Cl.²............... C07D 471/16; C07D 471/18
[58] Field of Search .......260/287 R, 287 P, 288 CF

[56] References Cited
UNITED STATES PATENTS

| | | | |
|---|---|---|---|
| 3,784,550 | 1/1974 | Yale | 260/287 R |
| 3,793,328 | 2/1974 | Hester | 260/287 R |

*Primary Examiner*—Alton D. Rollins
*Assistant Examiner*—David E. Wheeler
*Attorney, Agent, or Firm*—Stevens, Davis, Miller & Mosher

[57] ABSTRACT

Compounds of the formula:

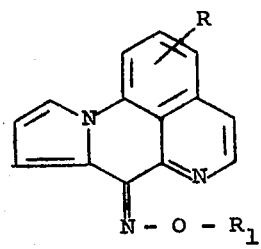

wherein R represents hydrogen, halogen or alkoxy of 1 to 4 carbon atoms, and $R_1$ represents hydrogen, alkyl of 1 to 4 carbon atoms substituted by (i) carboxy, (ii) alkoxycarbonyl in which the alkoxy moiety contains 1 to 7 carbon atoms, or (iii) carbamoyl, or $R_1$ represents phenylalkyl in which the alkyl moiety contains 1 to 4 carbon atoms and is substituted by (i) carboxy, (ii) alkoxycarbonyl in which the alkoxy moiety contains 1 to 4 carbon atoms, or (iii) carbamoyl, or $R_1$ represents alkanoyl of 1 to 4 carbon atoms or benzoyl, are new compounds possessing chemotherapeutic properties and are particularly active as antibilharzial, anthelmintic and antimicrobial agents.

11 Claims, No Drawings

7H-INDOLIZINO [5,6,7-IJ]ISOQUINOLINE DERIVATIVES

This invention relates to new therapeutically useful 7H-indolizino[5,6,7-ij]isoquinoline derivatives, to processes for their preparation and to pharmaceutical compositions containing them.

The 7H-indolizino[5,6,7-ij]isoquinoline derivatives of the present invention are those compounds of the general formula:

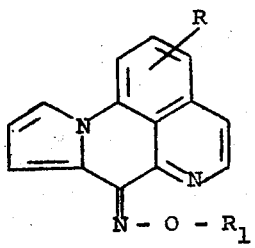

wherein R represents a hydrogen or halogen (preferably chlorine) atom, or an alkoxy radical containing 1 to 4 carbon atoms, and $R_1$ represents a hydrogen atom, an alkyl radical containing 1 to 4 carbon atoms substituted by (i) a carboxy radical, (ii) an alkoxycarbonyl radical in which the alkoxy moiety contains 1 to 7 carbon atoms, or (iii) a carbamoyl radical, or $R_1$ represents a phenylalkyl radical in which the alkyl moiety contains 1 to 4 carbon atoms and is substituted by (i) a carboxy radical, (ii) an alkoxycarbonyl radical in which the alkoxy moiety contains 1 to 4 carbon atoms or (iii) a carbamoyl radical, or $R_1$ represents an alkanoyl radical containing 1 to 4 carbon atoms or a benzoyl radical, and salts of those compounds wherein $R_1$ contains a carboxy radical.

According to a feature of the invention, the compounds of general formula I, wherein R is as hereinbefore defined and $R_1$ represents a hydrogen atom, an alkyl radical containing 1 to 4 carbon atoms substituted by a carboxy radical, an alkoxycarbonyl radical in which the alkoxy moiety contains 1 to 7 carbon atoms or a carbamoyl radical, or $R_1$ represents a phenylalkyl radical in which the alkyl moiety contains 1 to 4 carbon atoms and is substituted by a carboxy radical, an alkoxycarbonyl radical in which the alkoxy moiety contains 1 to 4 carbon atoms or a carbamoyl radical, are prepared by the process which comprises reacting a compound of the general formula:

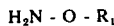

$H_2N - O - R_1$  II (wherein $R_1$ has the meaning just hereinbefore specified) with a 7H-indolizino[5,6,7-ij]isoquinolin-7-one of the general formula:

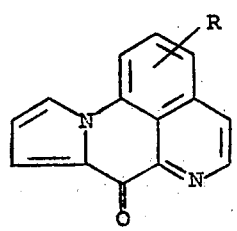

III wherein R is as hereinbefore defined. The reaction is generally carried out in an organic solvent, e.g. pyridine, optionally in the presence of other solvents such as alcohols, preferably ethanol, water or a mixture of said solvents, at the boiling point of the reaction mixture. It is particularly advantageous to use the compounds of general formula II in the form of an acid addition salt such as the hydrochloride.

According to another feature of the invention, the compounds of general formula I, wherein R is as hereinbefore defined and $R_1$ represents an alkanoyl radical containing 1 to 4 carbon atoms or a benzoyl radical, are prepared by the process which comprises reacting an acid of the general formula:

$R_2 - COOH$  IV (wherein $R_2$ represents a hydrogen atom, an alkyl radical containing 1 to 3 carbon atoms, or the phenyl radical) or a reactive derivative thereof, for example a halide or the anhydride, with a compound of general formula I wherein $R_1$ represents a hydrogen atom, viz. a compound of the general formula:

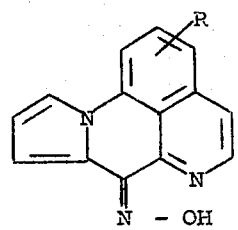

V wherein R is as hereinbefore defined. The reaction is generally carried out in an organic solvent, for example pyridine, at a temperature below 15°C. Preferably the anhydride of the acid of general formula IV is used.

According to another feature of the invention, the compounds of general formula I, wherein R is as hereinbefore defined and $R_1$ represents an alkyl radical containing 1 to 4 carbon atoms substituted by a carboxy radical, an alkoxycarbonyl radical in which the alkoxy moiety contains 1 to 7 carbon atoms or a carbamoyl radical, or $R_1$ represents a phenylalkyl radical in which the alkyl moiety contains 1 to 4 carbon atoms and is substituted by a carboxy radical, an alkoxycarbonyl radical in which the alkoxy moiety contains 1 to 4 carbon atoms, or a carbamoyl radical, are prepared by the process which comprises reacting a compound of the general formula:

$R_3 - X$  VI (wherein $R_3$ represents an alkyl radical containing 1 to 4 carbon atoms substituted by a carboxy radical, an alkoxycarbonyl radical in which the alkoxy moiety contains 1 to 7 carbon atoms, or a carbamoyl radical, or $R_3$ represents a phenylalkyl radical in which the alkyl moiety contains 1 to 4 carbon atoms and is substituted by a carboxy radical, an alkoxycarbonyl radical in which the alkoxy moiety contains 1 to 4 carbon atoms, or a carbamoyl radical, and X represents the acid residue of a reactive ester such as a halogen atom) with a quaternary ammonium salt, for example the tetraethylammonium salt, of an oxime of general formula V.

The tetraethylammonium salt of the oxime of general formula V is generally prepared in situ by reacting tetraethylammonium hydroxide with the oxime of general formula V, the reaction being carried out in an organic solvent such as an alcohol, e.g. methanol or ethanol, or in an aqueous-alcoholic medium.

The condensation of the reactive ester of general formula VI with the quaternary ammonium salt, e.g. the tetraethylammonium salt, of the oxime of general formula V is carried out in an organic solvent such as an alcohol, e.g. ethanol or methanol, an ester, e.g. ethyl acetate, or an amide, e.g. dimethylformamide, and optionally in the presence of water, at a temperature of between 0° and 30° C.

According to the invention, the compounds of general formula I, wherein R is as hereinbefore defined and $R_1$ represents an alkyl radical containing 1 to 4 carbon atoms substituted by an alkoxycarbonyl radical in which the alkoxy moiety contains 1 to 7 carbon atoms or a carbamoyl radical, or $R_1$ represents a phenylalkyl radical in which the alkyl moiety contains 1 to 4 carbon atoms and is substituted by an alkoxycarbonyl radical in which the alkoxy moiety contains 1 to 4 carbon atoms or a carbamoyl radical, are prepared from a compound of general formula I wherein $R_1$ represents an alkyl radical containing 1 to 4 carbon atoms substituted by a carboxy radical, or a phenylalkyl radical in which the alkyl moiety contains 1 to 4 carbon atoms and is substituted by a carboxy radical, viz. a compound of the general formula:

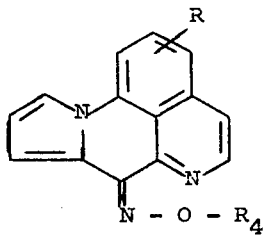

VII (wherein R is as hereinbefore defined and $R_4$ represents an alkyl radical containing 1 to 4 carbon atoms substituted by a carboxy radical, or a phenylalkyl radical in which the alkyl moiety contains 1 to 4 carbon atoms and is substituted by a carboxy radical) by methods known per se for converting a carboxy radical to an alkoxycarbonyl or carbamoyl radical without affecting the rest of the molecule. By the term "methods known per se" as used in this specification is meant methods heretofore used or described in the chemical literature.

In order to convert the carboxy radical to an alkoxycarbonyl radical, it is particularly advantageous to carry out a direct esterification of the acid of formula VII by means of an alcohol of the general formula:

$R_5OH$   VIII wherein, when $R_4$ represents an alkyl radical substituted by a carboxy radical, $R_5$ represents an alkyl radical containing 1 to 7 carbon atoms or, when $R_4$ represents a phenylalkyl radical in which the alkyl radical is substituted by a carboxy radical, $R_5$ represents an alkyl radical containing 1 to 4 carbon atoms, or to react an alkyl halide of the general formula:

$R_5Hal$   IX wherein $R_5$ is as hereinbefore defined and Hal represents a halogen atom, with a salt of the acid of formula VII formed with an alkali metal or quaternary ammonium ion. In order to prepare methyl esters of the acids, it is also possible to react diazomethane with the acid In order to convert the carboxy radical to a carbamoyl radical, it is particularly advantageous to react ammonia with the acid of formula VII dissolved in an organic solvent, for example dimethylformamide, in the presence of a condensation agent such as N,N'-carbonyldiimidazole.

According to a still further feature of the invention, the compounds of general formula I, wherein R is as hereinbefore defined and $R_1$ represents an alkyl radical containing 1 to 4 carbon atoms substituted by a carboxy radical, or a phenylalkyl radical in which the alkyl moiety contains 1 to 4 carbon atoms and is substituted by a carboxy radical, are prepared by the saponification of a compound of general formula I, wherein R is as hereinbefore defined and $R_1$ represents an alkyl radical containing 1 to 4 carbon atoms substituted by an alkoxycarbonyl radical in which the alkoxy moiety contains 1 to 7 carbon atoms, or a phenylalkyl radical in which the alkyl moiety contains 1 to 4 carbon atoms and is substituted by an alkoxycarbonyl radical in which the alkoxy moiety contains 1 to 4 carbon atoms, viz. a compound of the general formula:

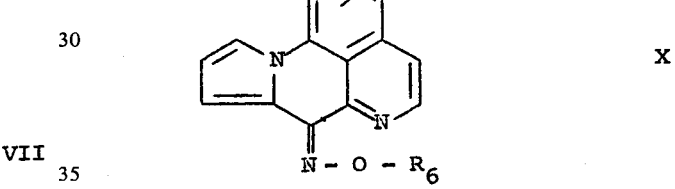

X wherein R is as hereinbefore defined and $R_6$ represents an alkyl radical containing 1 to 4 carbon atoms substituted by an alkoxycarbonyl radical in which the alkoxy moiety contains 1 to 7 carbon atoms, or a phenylalkyl radical in which the alkyl moiety contains 1 to 4 carbon atoms and is substituted by an alkoxycarbonyl radical in which the alkoxy moiety contains 1 to 4 carbon atoms. The saponification is generally carried out in an alkaline medium in the presence of sodium hydroxide or potassium hydroxide, and at a temperature between 0° and 30°C.

The 7H-indolizino[5,6,7-ij]isoquinolin-7-ones of general formula III can be prepared by alkaline hydrolysis of an imine of the general formula:

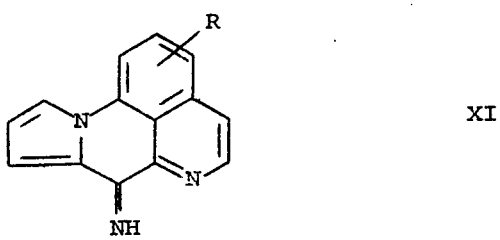

XI wherein R is as hereinbefore defined. The hydrolysis is generally carried out by heating the imine in an organic medium in the presence of aqueous sodium hydroxide.

The imines of general formula XI can be prepared by cyclisation of an isoquinoline derivative of the general formula:

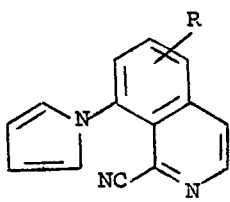

XII

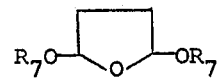

XV (wherein $R_7$ represents a methyl or ethyl radical) with an 8-aminoisoquinoline derivative of the general formula:

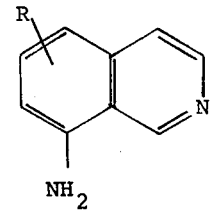

wherein R is as hereinbefore defined. Cyclisation of the isoquinoline derivative is generally carried out in an organic solvent, or a mixture of organic solvents, in the presence of a strong inorganic acid, for example hydrochloric acid, and at a temperature of about 0°C.

The isoquinoline derivatives of general formula XII can be prepared from compounds of the general formula:

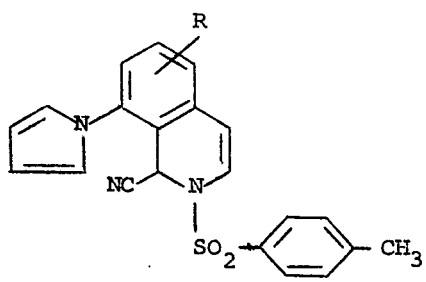

XIII wherein R is as hereinbefore defined. The reaction is generally carried out by stirring the compound of general formula XIII in an organic solvent, for example dimethylformamide, in the presence of an alkali metal hydride and at a temperature of about 20°C.

The dihydroisoquinoline derivatives of general formula XIII can be prepared by reacting an alkali metal cyanide and toluene-p-sulphonyl chloride with an isoquinoline derivative of the general formula:

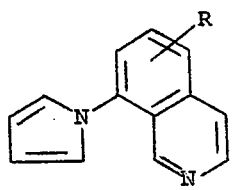

XIV wherein R is as hereinbefore defined.. The reaction is generally carried out in an aqueous-organic solvent medium, such as a mixture of water and methylene chloride, at a temperature of about 0°C.

The isoquinoline derivatives of general formula XIV can be prepared by reacting a tetrahydrofuran derivative of the general formula:

wherein R is as hereinbefore defined. The reaction is generally carried out in an organic solvent, for example acetic acid, at the boiling point of the reaction mixture.

The isoquinolines of general formula XVI can be prepared either by the method of Y. Ahmad and D. J. Hey, J. Chem. Soc., 3882 (1961) or by the method of R. Manske and M. Kulka, Can. J. Research, 27 B, 169 (1949).

The compounds of general formula I prepared according to the processes of the present invention can optionally be purified by physical methods such as crystallisation or chromatography.

The compounds of general formula I, wherein $R_1$ represents an alkyl radical substituted by a carboxy radical, or a phenylalkyl radical in which the alkyl moiety is substituted by a carboxy radical, can be converted into non-toxic metal salts or addition salts with nitrogenous bases by application of methods known per se. Thus, these salts can be prepared by the action of an alkali metal or alkaline earth metal base, ammonia or an amine, on an acid within general formula I in a suitable solvent such as an alcohol, an ether, a ketone or water; the salt formed is precipitated, if necessary after concentration of the solution, and is separated by filtration or decantation.

The new 7H-indolizino[5,6,7-ij]isoquinoline derivatives of general formula I and, when appropriate, salts thereof possess useful chemotherapeutic properties. They are particularly active as antibilharzial, anthelminthic and antimicrobial agents.

In mice infested with Schistosoma mansoni, the compounds have been found active at doses between 250 and 1,000 mg./kg. animal body weight per day administered orally, and between 125 and 250 mg./kg. animal body weight administered subcutaneously. In monkeys [Macaca mulatta (rhesus strain)] infested with Schistosoma mansoni, the activity of the compounds is particularly good at doses between 30 and 80 mg./kg. animal body weight administered orally.

The anthelminthic activity of compounds of general formula I is manifest particularly against Enterobii and Cestodes.

In vitro, the compounds of general formula I are active against Gram-positive microorganisms at concentrations between 10 and 100 μg./ml.

The 7H-indolizino[5,6,7-ij]isoquinoline derivatives of the general formula:

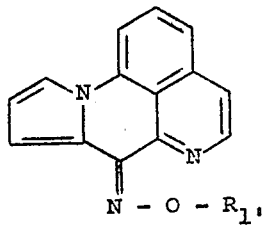

XVII wherein R₁, represents an alkyl radical containing 1 to 4 carbon atoms substituted by a carboxy radical or an alkoxycarbonyl radical in which the alkoxy moiety contains 1 to 7 carbon atoms, and salts thereof, are of outstanding interest. Examples of such compounds are 7-carboxymethoxyimino-7H-indolizino[5,6,7-ij]isoquinoline, 7-(1-carboxyethoxyimino)-7H-indolizino[5,6,7-ij]isoquinoline, 7-(1-carboxypropoxyimino)-7H-indolizino[5,6,7-ij]isoquinoline, 7-ethoxycarbonylmethoxyimino-7H-indolizino[5,6,7-ij]isoquinoline, 7-isopropoxycarbonylmethoxyimino-7H-indolizino[5,6,7-ij]isoquinoline, 7-(2-carboxyethoxyimino)-7H-indolizino[5,6,7-ij]isoquinoline, 7-methoxycarbonylmethoxyimino-7H-indolizino[5,6,7-ij]isoquinoline, 7-propoxycarbonylmethoxyimino-7H-indolizino[5,6,7-ij]isoquinoline, 7-pentyloxycarbonylmethoxyimino-7H-indolizino[5,6,7-ij]isoquinoline, 7-hexyloxycarbonylmethoxyimino-7H-indolizino[5,6,7-ij]isoquinoline, 7-heptyloxycarbonylmethoxyimino-7H-indolizino[5,6,7-ij]isoquinoline, 7-[(1- t-butoxycarbonyl-1-methylethoxy)imino]-7H-indolizino[5,6,7-ij]isoquinoline, 7-(1-ethoxycarbonylpropoxyimino)-7H-indolizino[5,6,7-ij]isoquinoline, 7-(1-ethoxycarbonylethoxyimino)-7H-indolizino[5,6,7-ij]isoquinoline, 7-(1-ethoxycarbonylbutoxyimino)-7H-indolizino[5,6,7-ij]isoquinoline, 7-(1-ethoxycarbonyl-1-methylethoxyimino)-7H-indolizino[5,6,7-ij]isoquinoline, 7-(1-carboxy-1-methylethoxyimino)-7H-indolizino[5,6,7-ij]isoquinoline and 7-(1-carboxybutoxyimino)-7H-indolizino[5,6,7-ij]isoquinoline. The preferred compounds are 7-carboxymethoxyimino-7H-indolizino[5,6,7-ij]isoquinoline, 7-(1-carboxyethoxyimino)-7H-indolizino[5,6,7-ij]isoquinoline, 7-ethoxycarbonylmethoxyimino-7H-indolizino[5,6,7-ij]isoquinoline and 7-methoxycarbonylmethoxyimino-7H-indolizino[5,6,7-ij]isoquinoline, For use in human or veterinary therapy the compounds of general formula I can be used as such or, when appropriate, in the form of pharmaceutically-acceptable salts, i.e. salts which are non-toxic to the animal organism in therapeutic doses of the salts.

The following Examples illustrate the preparation of compounds of the present invention.

EXAMPLE 1

A solution of 7H-indolizino[5,6,7-ij]isoquinolin-7-one (28 g.) and hydroxylamine hydrochloride (28 g.) in pyridine (560 cc.) is maintained at the boiling point, with stirring. The brown solution thus obtained is poured into water (3.92 liters). After stirring for 3 hours, the mustard yellow crystals obtained are filtered off and then washed copiously with water. After drying, 7-hydroxyimino-7H-indolizino[5,6,7-ij]isoquinoline (27.2 g.), melting at 254°C. with decomposition, is obtained. After recrystallisation from a mixture of water and pyridine (6–5 by volume), the pure product melts at 258°C. with decomposition.

7H-Indolizino[5,6,7-ij]isoquinolin-7-one, used as starting material, can be prepared in the following way:

The 7-Imino-7H-indolizino[5,6,7-ij]isoquinoline (110 g.) and N sodium hydroxide solution ( cc.) in ethanol (4.4 liters) and water (4.4 liters) are heated under reflux for 4 hours. After cooling, 7H-indolizino[5,6,7-ij]isoquinolin-7-one (108.1 g.) is obtained in the form of yellow needles melting at 264°C.

7-Imino-7H-indolizino[5,6,7-ij]isoquinoline can be prepared in the following way:

A solution of 1-cyano-8-(pyrrol-1-yl)isoquinoline (279 g.) in diethyl ether (7 liters) and pure chloroform (7 liters) saturated with anhydrous hydrogen chloride is kept at a temperature of between 0° and 5°C. for 72 hours. After extraction with ice-water (15 liters) followed by alkalinisation of the blood red acid solution thus obtained, 7-imino-7H-indolizino[5,6,7-ij]isoquinoline (223.4 g.) is obtained in the form of green-yellow needles melting at 201°C. with decomposition.

1-Cyano-8-(pyrrol-1-yl)isoquinoline can be prepared in the following way:

A mixture of 1-cyano-8-(pyrrol-1-yl)-2-toluene- p-sulphonyl-1,2-dihydroisoquinoline (446.2 g.) and sodium hydride (50% dispersion in mineral oil) (68.7 g.) in dimethylformamide (2,232 cc.) is kept at a temperature of about 20°C. for 16 hours. Crude 1-cyano-8-(pyrrol-1-yl)isoquinoline (261 g.), melting at 178°C., is thus obtained.

1-Cyano-8-(pyrrol-1-yl)-2-toluene-p-sulphonyl-1,2-dihydroisoquinoline can be prepared in the following way:

8-(Pyrrol-1-yl)isoquinoline (293 g.) and potassium cyanide (295 g.) are dissolved in a mixture of methylene chloride (880 cc.) and water (880 cc.) and the solution stirred at a temperature of between 0° and 5°C. After adding a solution of toluene-p-sulphonyl chloride (575 g.) in methylene chloride (880 cc.) over the course of 45 hours, decanting and then washing the organic solution with water, a solid brown residue is obtained. After recrystallisation from acetonitrile (750 cc.), this crude product yields 1-cyano-8-(pyrrol-1-yl)-2-toluene-p-sulphonyl-1,2-dihydroisoquinoline (407 g.) melting at 160°C.

After washing with sodium hydroxide solution, the mother liquors yield 1-cyano-8-(pyrrol-1-yl)-2-toluene-p-sulphonyl-1,2-dihydroisoquinoline (a further 39.3 g.) melting at 160°C.

8-(Pyrrol-1-yl)isoquinoline can be prepared in the following way:

2,5-Diethoxytetrahydrofuran (300 g.) is added over the course of 6 minutes to a boiling solution of 8-aminoisoquinoline (245 g.) in acetic acid (1.25 liters). After rendering the solution alkaline by means of sodium hydroxide solution (2.2 liters), a brown solid (327 g.), melting at 90°C., is obtained. This crude product is dissolved in a mixture of ethyl acetate (1.55 liters) and cyclohexane (1.55 liters). After filtering through a column containing alkaline alumina (3.3 kg.) and then evaporating the solvents, 8-(pyrrol-1-yl)isoquinoline (294 g.), melting at 91°C., is obtained.

8-Aminoisoquinoline can be prepared according to Y. Ahmad and D. J. Hey, J. Chem. Soc., 3882 (1961).

EXAMPLE 2

A solution of aminooxyacetic acid hemihydrochloride (60.0 g.) in water (180 cc.) is added to a stirred boiling solution of 7H-indolizino 5,6,7-ij]isoquinolin-7-one (60.0 g.) in ethanol (1,800 cc.) and pyridine (27.3 cc.). Boiling is maintained for 2 hours 30 minutes. After cooling, the yellow crystals obtained are filtered off, washed with 90% ethanol, then with absolute ethanol and finally with diethyl ether. After drying, 7-carboxymethoxyimino-7H-indolizino[5,6,7-ij]isoquinoline (67.6 g.), melting at 212°C. with decomposition, is obtained.

EXAMPLE 3

A solution of 2-aminooxypropionic acid hydrochloride (15.0 g.) in water (37.5 cc.) is added to a stirred boiling solution of 7H-indolizino[5,6,7-ij]isoquinolin-7-one (15.0 g.) in ethanol (375 cc.) and pyridine (8.14 g.). Boiling is maintained for 2 hours 30 minutes. After cooling, the orange crystals are filtered off, washed with 90% ethanol, then with absolute ethanol and finally with diethyl ether. After drying, 7-(1-carboxyethoxyimino)-7H-indolizino[5,6,7-ij]isoquinoline (16.0 g.), melting at 225°C. with decomposition, is obtained.

EXAMPLE 4

Following the procedure of Example 3 but starting with 7H-indolizino[5,6,7isoquinolin-7-one (14.33 g.) dissolved in ethanol (430 cc.) and pyridine (7.5cc.) and with 2-aminooxybutyric acid hydrochloride (14.33 g.) dissolved in water (43 cc.), 7-(1-carboxypropoxyimino -7H-indolizino[5,6,7-ij]isoquinoline (11.92 g.), melting at 180°C. with decomposition, is obtained.

EXAMPLE 5

A solution of α-aminooxyphenylacetic acid hydrochloride (15.0 g.) in water (6.6 cc.) is added to a stirred boiling solution of 7H-indolizino[5,6,7-ij]isoquinoline-7-one (15.0 g.) in ethanol (450 cc.) and pyridine (583 g.). Boiling is maintained for 2 hours 30 minutes. After cooling, the yellow crystals obtained are filtered off and then washed with 90% ethanol, then with absolute ethanol and finally with diethyl ether. After drying, 7-(α-carboxybenzyloxyimino)-7H-indolizino[5,6,7-ij]isoquinoline (17.7 g.), melting at 200° C. with decomposition, is obtained.

EXAMPLE 6

A solution of ethyl aminooxyacetate hydrochloride (18.0 g.) in water (64 cc.) is added to a stirred boiling solution of 7H-indolizino[5,6,7-ij]isoquinolin-7-one (16.0 g.) in ethanol (320 cc.) and pyridine (9.1 g.). Boiling is maintained for 3 hours 30 minutes. After cooling, water (640 cc.) is added. The greenish yellow crystals thus obtained are filtered off and washed with 25% ethanol and then with water. After drying, crude 7-ethoxycarbonylmethoxyimino-7H-indolizino[5,6,7-ij isoquinoline (21.6 g.) is obtained and is recrystallised from a mixture of ethyl acetate (110 cc.) and cyclohexane (165 cc.). 7-Ethoxycarbonylmethoxyimino-7H-indolizino[5,6,7-ij]isoquinoline (13.1 g.), melting at 134° C., is thus obtained.

EXAMPLE 7

A solution of isopropyl aminooxyacetate hydrochloride (23.4 g.) in water (128 cc.) is added to a stirred boiling suspension of 7H-indolizino[5,6,7-ij]isoquinolin-7-one (16.0 g.) in ethanol (320 cc.) and pyridine (11.05 g.). Boiling is maintained for 2 hours 45 minutes. After cooling to a temperature of about 20° C., water (960 cc.) is added with stirring. After stirring for 16 hours, the brown amorphous product which has precipitated is filtered off, then washed with distilled water and dissolved in ethyl acetate (500 cc.). The resulting organic solution is washed with water (3 × 200 cc.) and then dried over calcined magnesium sulphate. After evaporation of the solvent under reduced pressure, crude 7-isopropoxycarbonylmethoxyimino-7H-indolizino[5,6,7-ij]isoquinoline (18.1 g.) is obtained and is recrystallised from a mixture of ethyl acetate (115 cc.) and cyclohexane (460 cc.). 7-Isopropoxycarbonylmethoxyimino-7H-indolizino[5,6,7-ij]isoquinoline, solvated by ethyl acetate, (12.49 g.), melting at 70° C., is thus obtained.

EXAMPLE 8

A solution of 3-aminooxypropionic acid hydrochloride (12 g.) in water (36 cc.) is added to a stirred boiling solution of 7H-indolizino[5,6,7-ij]isoquinolin-7-one (12 g.) in ethanol (360 cc.) and pyridine (6.64 g.). Boiling is maintained for 3 hours 10 minutes. After cooling, the yellow crystals obtained are filtered off and then washed with 90% ethanol, with absolute ethanol and finally with diethyl ether. After drying, 7-(2-carboxyethoxyimino)-7H-indolizino[5,6,7-ij]isoquinoline (12.59 g.), melting at 250° C. with decomposition, is obtained.

EXAMPLE 9

Following the procedure of Example 1 but starting with 1-methoxy-7H-indolizino[5,6,7-ij]isoquinolin-7-one (40 g.) and hydroxylamine hydrochloride (40 g.) in pyridine (800 cc.), 7-hydroxyimino-1-methoxy-7H-indolizino[5,6,7-ij]isoquinoline (33.3 g.), melting at 264° C. with decomposition, is obtained. After recrystallisation from a mixture of water and pyridine (2.7-1 by volume), the purified product melts at 226° C. with decomposition.

1-Methoxy-7H-indolizino[5,6,7-ij]isoquinolin-7-one, which melts at 217° C. and was used as starting material, can be prepared in the same way as 7H-indolizino[5,6,7-ij]isoquinolin-7-one by forming the following compounds as intermediates:

7-imino-1-methoxy-7H-indolizino[5,6,7-ij]isoquinoline melting at 172° C.,
1-cyano-7-methoxy-8-(pyrrol-1-yl)isoquinoline melting at 246° C.,
1-cyano-7-methoxy-8-(pyrrol-1-yl)-2-toluene-p-sulphonyl- 1,2-dihydroisoquinoline melting at 129° C.,
7-methoxy-8-(pyrrol-1-yl)isoquinoline melting at 112° C., and
8-amino-7-methoxyisoquinoline melting at 156° C. [prepared in accordance with the method of Y. Ahmad and D. J. Hey, J. Chem. Soc., 3882 (1961)].

EXAMPLE 10

Following the procedure of Example 2 but starting with 1-methoxy-7H-indolizino[5,6,7-ij]isoquinolin-7-one (24 g.) and aminooxyacetic acid hemi-hydrochloride (24 g.), 7-carboxymethoxyimino-1-methoxy-7H-indolizino[5,6,7-ij]-isoquinoline (11.9 g.), melting at 162° C. with decomposition, is prepared.

EXAMPLE 11

Following the procedure of Example 1 but starting with 3-chloro-7H-indolizino[5,6,7-ij]isoquinolin-7-one (14.5 g.) and hydroxylamine hydrochloride (14.5 g.) in pyridine (480 cc.), crude 3-chloro-7-hydroxyimino- 7H-indolizino[5,6,7-ij]isoquinoline (14.1 g.) is prepared. After recrystallisation from a mixture of dioxan and water (2–3 by volume) (275 parts:v/w), the product is in the form of green-yellow crystals melting at 260° C. with decomposition.

3-Chloro-7H-indolizino[5,6,7-ij]isoquinolin-7-one, which melts at 315° C. and was used as starting material can be prepared in the same way as 7H-indolizino[5,6,7-ij]isoquinolin-7-one by forming the following compounds as intermediates:

3-chloro-7-imino-7H-indolizino[5,6,7-ij]isoquinoline melting at 242° C., 5-chloro-1-cyano-8-(pyrrol-1-yl)isoquinoline melting at 151° C., 5-chloro-1-cyano-8-(pyrrol-1-yl)-2-toluene-p-sulphonyl-1,2-dihydroisoquinoline melting at 142° C., 5-chloro-8-(pyrrol-1-yl)isoquinoline melting at 111° C., and 8-amino-5-chloroisoquinoline melting at 205° C. [prepared in accordance with the method of Y. Ahmad and D. J. Hey, J. Chem. Soc., 3882 (1961)].

EXAMPLE 12

Following the procedure of Example 2 but starting with 3-chloro-7H-indolizino[5,6,7-ij]isoquinolin-7-one (1.02 g.) and ethyl aminooxyacetate hydrochloride (0.89 g.), 3-chloro-7-ethoxycarbonylmethoxyimino-7H-indolizino-[5,6,7-ij]isoquinoline (0.45 g.), melting at 175° C., is obtained.

EXAMPLE 13

Following the procedure of Example 1 but starting with 1-chloro-7H-indolizino[5,6,7-ij]isoquinolin-7-one (14.03 g.) and hydroxylamine hydrochloride (14.03 g.) in pyridine (285 cc.), crude 1-chloro-7-hydroxyimino-7H-indolizino[5,6,7-ij]isoquinoline (18.5 g.) is obtained. After recrystallisation from a mixture of pyridine and dioxan (8–5 by volume) (70 parts: v/w), the product is in the form of green-brown crystals melting at 272° C. with decomposition.

1-Chloro-7H-indolizino[5,6,7-ij]isoquinolin-7-one, which melts at 220° C. and was used as starting material, can be prepared in the same way as 7H-indolizino[5,6,7-ij]isoquinolin-7-one by forming the following compounds as intermediates:

1-chloro-7-imino-7H-indolizino[5,6,7-ij]isoquinoline melting at 210° C., 7-chloro-1-cyano-8-(pyrrol-1-yl)isoquinoline melting at 176° C., 7-chloro-1-cyano-8-(pyrrol-1-yl)-2-toluene-p-sulphonyl-1,2-dihydroisoquinoline melting at 155° C., 7-chloro-8-(pyrrol-1-yl)isoquinoline melting at 149° C., and 8-amino-7-chloro-isoquinoline melting at 172° C. [prepared in accordance with the method of R. Manske and M. Kulka, Can. J. Research, 27 B, 161 (1949)].

EXAMPLE 14

Acetic anhydride (20 cc.) is added, over the course of 5 minutes, to a stirred suspension of 7-hydroxyimino-7H-indolizino[5,6,7-ij]isoquinoline (10 g.) in pyridine (100 cc.) kept at between 8° and 10° C. A brown solution is thus obtained. After stirring for 5 minutes at 10° C., the acetic acid ester crystallises. The mixture is kept at ambient temperature for a further 2 hours and then water (600 cc.) is added. The ochre-yellow crystals thus obtained are filtered off and washed copiously with water. After drying, 7-acetyloxyimino-7H-indolizino[5,6,7-ij]isoquinoline (11.0 g.), melting at 177°–179° C. with decomposition, is obtained.

After recrystallisation from ethanol (40 parts:v/w), the pure product melts at 181° C. with decomposition.

EXAMPLE 15

Following the procedure of Example 14 but starting with 1-chloro-7-hydroxyimino-7H-indolizino-[5,6,7-ij]isoquinoline (18.13 g.), pyridine (181 cc.) and acetic anhydride (36.2 cc.), crude 7-acetyloxyimino-1-chloro-7H-indolizino[5,6,7-ij]isoquinoline (19.9 g.), melting at about 180° C. with decomposition, is obtained. After recrystallisation from methyl ethyl ketone (12.5 parts: v/w), the pure product melts at 186° C. with decomposition.

EXAMPLE 16

Benzoic anhydride (30 cc.) is added to a stirred suspension of 7-hydroxyimino-7H-indolizino[5,6,7-ij]isoquinoline (15 g.) in pyridine (150 cc.) kept at between 8° and 10° C. After stirring for 5 minutes at 10° C., a brown solution is obtained in which crystals of the benzoic acid ester rapidly appear. The mixture is kept at ambient temperature for 6 hours and then water (900 cc.) is added. The green-yellow crystals thus obtained are filtered off and washed copiously with water. After drying, 7-benzoyloxyimino-7H-indolizino-[5,6,7-ij]isoquinoline (31.2 g.) is obtained. After recrystallisation from methyl ethyl ketone (10 parts: v/w), the pure product melts at 227° C. with decomposition.

EXAMPLE 17

Following the procedure of Example 16 but starting with 7-hydroxyimino-1-methoxy-7H-indolizino-[5,6,7-ij]isoquinoline (13.05 g.), pyridine (130.5 cc.) and benzoic anhydride (26.1 g.), crude 7-benzoyloxyimino-1-methoxy-7H-indolizino[5,6,7-ij]isoquinoline (17.8 g.), melting at about 140° C. with decomposition, is obtained. After recrystallisation from methyl ethyl ketone (50 parts: v/w), the pure product melts at 197° C. with decomposition.

EXAMPLE 18

A 0.57M solution of diazomethane in diethyl ether (108 cc.) is added to a suspension of 7-carboxymethoxyimino-7H-indolizino[5,6,7-ij]isoquinoline (15 g.) in dimethylformamide (150 cc.) cooled to 0° C. The mixture is kept at between 0° and 5° C. for 3 hours and is then allowed to return to a temperature of about 20° C. Water (450 cc.) is then added, the mixture is cooled in an ice-water bath and the yellow crystals thus obtained are filtered off. After drying, the crude methyl ester (14.17 g.) is obtained. After recrystallisation from ethyl acetate (280 cc.), the 7-methoxycarbonylmethoxyimino-7H-indolizino[5,6,7-ij]isoquinoline obtained melts at 148 °C. with decomposition.

EXAMPLE 19

A 0.55M solution of diazomethane in diethyl ether (151 cc.) is added to a solution of 7-carboxymethoxyimino-1-chloro-7H-indolizino[5,6,7-ij]isoquinoline (21 g.) in dimethylformamide (255 cc.) cooled to 0°C. The reaction mixture is kept at between 0° and 5°C. for 3 hours and is then allowed to return to a temperature of about 20°C. The solvent is evaporated under reduced pressure; the resulting residue is taken up in water (1 litre) and then extracted with methylene chloride (2 × 1 litre). The organic extracts are dried over calcined magnesium sulphate and treated with decolourising charcoal.

After filtration and evaporation of the solvent, the crystalline residue is taken up in boiling methanol (2,900 cc.) to which decolourising charcoal has been added. After effecting a hot filtration and then cooling, the crystals obtained are filtered off and dried under reduced pressure. 7-Methoxycarbonylmethoxyimino-1-chloro-7H-indolizino[5,6,7-ij]isoquinoline (19.73 g.) is thus obtained in the form of yellow crystals melting at 194°C.

EXAMPLE 20

A 17.5% (w/v) aqueous solution of tetraethylammonium hydroxide (42.1 cc.) is added to a suspension of 7-carboxymethoxyimino-7H-indolizino[5,6,7-ij]isoquinoline (14.7 g.) in ethanol (350 cc.). The ethanol is removed by evaporation at 40°C. under reduced pressure and the oily brown concentrate is taken up in dimethylformamide (200 cc.). n-Propyl iodide (5.35 cc.) is added to the stirred brown solution and the mixture is kept at a temperature of about 20°C. for 3 days. Water (1,600 cc.) is then added and the gummy precipitate is extracted with methylene chloride (total 1 litre). The organic solution is washed with water (2 × 500 cc.), dried over magnesium sulphate and then treated with decolourising charcoal. After filtration, the solvent is evaporated under reduced pressure and a residue (16.8 g.) is obtained. After recrystallisation from ethyl acetate (85 cc.), 7-propoxycarbonylmethoxyimino-7H-indolizino[5,6,7-ij]isoquinoline (11.15 g.), melting at 122°C., is obtained.

EXAMPLE 21

A 17.5% (w/v) aqueous solution of tetraethylammonium hydroxide (42.1 cc.) is added to a suspension of 7-carboxymethoxyimino-7H-indolizino[5,6,7-ij]isoquinoline (14.7 g.) in ethanol (350 cc.). The ethanol is removed by evaporation at 40°C. under reduced pressure and the oily brown concentrate is taken up in dimethylformamide (200 cc.). 1-Bromopentane (8.3 g.) is added dropwise, with stirring, to the brown solution and the mixture kept at a temperature of about 20°C. for 16 hours. Water (700 cc.) is then added slowly to start crystallisation. After stirring for 1 hour, the crystals are filtered off. After drying, 7-pentyloxycarbonyl-methoxyimino-7H-indolizino[5,6,7-ij]isoquinoline (16.16 g.), melting at 120°C., is obtained. After recrystallisation from acetonitrile, the pure product melts at 124°C.

EXAMPLE 22

Following the procedure of Example 21 but starting with 7-carboxymethoxyimino-7H-indolizino[5,6,7-ij]isoquinoline (11 g.), ethanol (260 cc.), a 17.5% (w/v) aqueous solution of tetraethylammonium hydroxide (34.8 cc.) and then dimethylformamide (150 cc.) and 1-iodohexane (8.75 g.), crude 7-hexyloxy-carbonylmethoxyimino[5,6,7-ij]isoquinoline (13.6 g.) is obtained. After recrystallisation from cyclohexane (136 cc.) and treatment with decolourising charcoal, the pure product melts at 100°C.

EXAMPLE 23

Following the procedure of Example 21 but starting with 7-carboxymethoxyimino-7H-indolizino[5,6,7-ij]isoquinoline (11 g.) in ethanol (260 cc.) and a 17.5% (w/v) aqueous solution of tetraethylammonium hydroxide (34.8 cc.) and then dimethylformamide (150 cc.) and 1-bromoheptane (7.4 g.), an oil is obtained after adding water (800 cc.), and this oil is extracted with diethyl ether (total 2 litres). The organic solution is washed with distilled water (total 300 cc.) and is then dried over anhydrous sodium sulphate. The solvent is evaporated under reduced pressure and 7-heptyloxycarbonylmethoxyimino-7H-indolizino[5,6,7-ij]isoquinoline (12.82 g.) is obtained in the form of a red oil. After chromatography on a silica gel column, eluting with a mixture of methylene chloride and cyclohexane (1-1by volume), a product (9.67 g.) is obtained which has the appearance of a wax which crystallises and melts at 98°C.

EXAMPLE 24

N,N'-carbonyldiimidazole (12.44 g.) is added to a stirred suspension of 7-carboxymethoxyimino-7H-indolizino[5,6,7,-ij]isoquinoline (15.0 g.) in anhydrous dimethylformamide (150 cc.). The mixture is stirred at a temperature of about 20°C. until the evolution of carbon dioxide ceases. After 5 to 10 minutes of contact, imidazolide crystals are deposited gradually from the resulting brown solution. After 2 hours of contact a stream of ammonia is bubbled through the reaction mixture. The temperature rises to 45°C. and an abundant precipitate forms. The bubbling of ammonia is continued for 3 hours and then the mixture is left to stand for 16 hours at a temperatue of about 20°C. The resulting suspension is poured into water (400 cc.) and then the yellow crystals of amide are filtered off, washed copiously with water and dried. 7-Carbamoylmethoxyimino-7H-indolizino[5,6,7-ij]isoquinoline (14.17 g.), melting at 252°C. with decomposition, is obtained.

After recrystallisation from a mixture of dimethylformamide and ethanol (2-1 by volume), the pure product is obtained in the form of green-yellow flakes melting at 270°C. with decomposition.

EXAMPLE 25

A 40% (w/v) solution of benzyltrimethylammonium hydroxide ("Triton B") in methanol (0.960 g.) is added to a suspension of 7-carboxymethoxyimino-7H-indolizino-[5,6,7-ij]isoquinoline (0.686 g.) in methanol (13.7 cc.). The mixture is heated to about 50°C. in order to achieve complete dissolution, and then the methanol is evaporated under reduced pressure. The quaternary ammonium salt thus obtained is suspended in dimethylformamide (12 cc.). Ethyl iodide (0.360 g.) is added to this suspension, which is then heated to about 40°C. in order to achieve complete dissolution. The solution is left to stand at a temperature of about 20°C. for 16 hours. Water (30 cc.) is added, the ester formed is extracted with methylene chloride, and the organic extracts are washed with water and then dried over calcined magnesium sulphate. The solvent is evaporated under reduced pressure and the brown-yellow oil obtained is taken up in water (10 cc.). The yellow crystals of the ethyl ester so formed are filtered off and washed copiously with water. After drying, 7-ethoxycarbonylmethoxyimino-7H-indolizino[5,6,7-ij]isoquinoline (0.580 g.), melting at 134°C., is obtained.

EXAMPLE 26

A 17.5% (w/v) aqueous solution of tetraethylammonium hydroxide (75.8 cc.) is added to a suspension of 7-hydroxyimino-7H-indolizino[5,6,7-ij]isoquinoline (20 g.) in ethanol (400 cc.). The ethanol is removed by evaporation at 40°C. under reduced pressure and the oily brown concentrate is taken up in dimethylformamide (240 cc.). Ethyl bromoacetate (15.03 g.) is added, over the course of 10 minutes, to the brown solution which is stirred and cooled to about 10°C., and the mixture is then kept at a temperature of about 20°C. for 16 hours. Ice-water (1,440 cc.) is then added and the precipitate is extracted with ethyl acetate (total 1 liter). The organic solution is washed with distilled water (total 600 cc.) and is then dried over anhydrous magnesium sulphate. The solvent is evaporated under reduced pressure and crude 7-ethoxycarbonylmethoxyimino-7H-indolizino[5,6,7-ij]isoquinoline (26.2 g.) is thus obtained in the form of a partially crystalline solid. After purification by chromatography on a column of silica gel, 7-ethoxycarbonylmethoxyimino- 7H-indolizino[5,6,7-ij]isoquinoline (14.3 g.), melting at 134°C., is obtained.

EXAMPLE 27

Following the procedure of Example 26 but starting with 7-hydroxyimino-7H-indolizino[5,6,7-ij]isoquinoline (23.5 g.), a 17.5% (w/v) aqueous solution of tetraethylammonium hydroxide (90 cc.) and t-butyl 2-bromoisobutyrate (23.4 g.) in dimethylformamide (500 cc.), 7-[(1-t-butoxycarbonyl-1-methylethoxy)imino]-7H-indolizino[5,6,7-ij]isoquinoline (35 g.) is obtained. After recrystallisation from acetonitrile (50 cc.), the product (28.9 g.) melts at 158°C.

EXAMPLE 28

A 17.5% (w/v) aqueous solution of tetraethylammonium hydroxide (50.5 cc.) is added to a stirred suspension of 3-chloro-7-hydroxyimino-7H-indolizino[5,6,7-ij]isoquinoline (16.2 g.) in dimethylformamide (210 cc.). The resulting brown solution is cooled to about 10°C. and then in one lot ethyl bromoacetate (23.16 g.) is added. The reaction mixture is left to stand at a temperature of about 20°C. for 4 hours and then distilled water (1.8 liters) is added. The resulting dark green precipitate is filtered off and washed copiously with water. The moist crude product is taken up in methylene chloride (2 liters) and the solution obtained is dried over anhydrous magnesium sulphate. After removing the solvent under reduced pressure, crude 3-chloro-7-ethoxycarbonylmethoxyimino-7H-indolizino[5,6,7-ij]isoquinoline (16 g.), melting at 172°C., is obtained. After recrystallisation from ethyl acetate (720 cc.), the pure product (11.36 g.) melts at 178°C.

EXAMPLE 29

Following the procedure of Example 28 but starting with 7-hydroxyimino-7H-indolizino[5,6,7-ij]isoquinoline (15 g.), dimethylformamide (180 cc.), a 17.5% (w/v) aqueous solution of tetraethylammonium hydroxide (55 cc.) and ethyl 2-bromobutyrate (12.7 g.), crude 7-(1-ethoxycarbonylpropoxyimino)-7H-indolizino[5,6,7-ij]isoquinoline (17.7 g.), melting at 148°C., is obtained.

After recrystallisation from ethyl acetate (20 parts: v/w), the pure product melts at 148°C.

EXAMPLE 30

Following the procedure of Example 28 but starting with 7-hydroxyimino-7H-indolizino[5,6,7-ij]isoquinoline (17 g.), dimethylformamide (170 cc.), a 17.5% (w/v) aqueous solution of tetraethylammonium hydroxide (63.8 cc.) and ethyl 2-bromopropionate (13.72 g.), crude 7-(1-ethoxycarbonylethoxyimino)-7H-indolizino[5,6,7-ij]isoquinoline (17.55 g.), melting at 150°C., is obtained. After recrystallisation from a mixture of ethyl acetate and cyclohexane (1–1 by volume) (28 parts:v/w), the pure product melts at 155°C.

EXAMPLE 31

Following the procedure of Example 28 but starting with 7-hydroxyimino-7H-indolizino[5,6,7-ij]isoquinoline (20 g.), dimethylformamide (255 cc.), a 17.5% (w/v) aqueous solution of tetraethylammonium hydroxide (75.3 cc.) and ethyl 2-bromo-3-phenylpropionate (23 g.), crude 7-(1-ethoxycarbonyl-2-phenylethoxyimino)-7H-indolizino[5,6,7-ij]isoquinoline (13.37 g.), melting at 110°C., is obtained.

After recrystallisation from a mixture of ethyl acetate and di-isopropyl ether (1–1 by volume) (3 parts:v/w), the pure product melts at 115°C.

EXAMPLE 32

Following the procedure of Example 28 but starting with 7-hydroxyimino-7H-indolizino[5,6,7-ij]isoquinoline (17 g.), dimethylformamide (170 cc.), a 17.5% (w/v) aqueous solution of tetraethylammonium hydroxide (63.8 cc.) and ethyl 2-bromovalerate (15.85 g.), crude 7-(1-ethoxycarbonylbutoxyimino)-7H-indolizino[5,6,7-ij]isoquinoline (17.5 g.), melting at 110°C., is obtained. After recrystallisation from a mixture of di-isopropyl ether and ethyl acetate (9–1 by volume) (4 parts:v/w), the pure product melts at 110°C.

EXAMPLE 33

Following the procedure of Example 28 but starting with 7-hydroxyimino-7H-indolizino[5,6,7-ij]isoquinoline (15 g.), dimethylformamide (180 cc.), a 17.5% (w/v) aqueous solution of tetraethylammonium hydroxide (55 cc.) and ethyl 2-bromo-isobutyrate (12.7 g.), crude 7-(1-ethoxycarbonyl-1-methylethoxyimino)-7H-indolizino[5,6,7-ij]isoquinoline (18.77 g.), melting between 150° and 155°C., is obtained. After recrystallisation from a mixture of ethyl acetate and cyclohexane (1–1 by volume), the pure product melts at 154°C.

EXAMPLE 34

To a stirred suspension of 3-chloro-7-ethoxycarbonylmethoxyimino-7H-indolizino[5,6,7-ij]isoquinoline (0.356 g.) in ethanol (15 cc.) there is added N sodium hydroxide solution (1 cc.) followed by distilled water (35 cc.). After stirring for 1 hour at a temperature of about 20°C., a dark green solution is obtained which is neutralised by adding N hydrochloric acid (1 cc.). The resulting precipitate is filtered off, washed copiously with water and dried under reduced pressure. 3-Chloro-7-carboxymethoxyimino-7H-indolizino[5,6,7-ij]isoquinoline (0.28 g.), melting at 202°C. with decomposition, is thus obtained.

EXAMPLE 35

Following the procedure of Example 34 but starting with 7-(1-ethoxycarbonylpropoxyimino)-7H- indolizino[5,6,7-ij]isoquinoline (8.24 g.), water (82.4 cc.) and N sodium hydroxide solution (25 cc.), 7-(1-carboxypropoxyimino)-7H-indolizino[5,6,7-ij]isoquinoline (6.72 g.), melting at 180°C. with decomposition, is obtained.

EXAMPLE 36

Following the procedure of Example 34 but starting with crude 7-(1-ethoxycarbonyl-1-methylexthoxyimino)-7H-indolizino[5,6,7-ij]isoquinoline (18.77 g.), ethanol (282 cc.) and N sodium hydroxide solution (55 cc.), the sodium salt of 7-(1-carboxy-1-methylethoxyimino)-7H-indolizino[5,6,7-ij]isoquinoline (14.07 g.), which crystallises from the hydrolysis medium, is obtained.

Ethanol (154 cc.) is added to a filtered solution of this sodium salt (15.43 g.) in distilled water (308 cc.), and then the mixture is acidified by adding N hydrochloric acid (44.9 cc.). The acid which precipitates is filtered off and washed successively with a mixture of ethanol and water (66–34 by volume), absolute ethanol and diethyl ether. After drying under reduced pressure, pure 7-(1-carboxy-1-methylethoxyimino)-7H-indolizino[5,6,7-ij]isoquinoline (14.21 g.), melting at 220°C. with decomposition, is obtained.

EXAMPLE 37

Following the procedure of Example 34 but starting with 7-(1-ethoxycarbonylbutoxyimino)7H-indolizino[5,6,7-ij]isoquinoline (16.48 g.), ethanol (330 cc.) and N sodium hydroxide solution (50 cc.), the sodium salt of 7-(1-carboxybutoxyimino-7H-indolizino[5,6,7-ij]isoquinoline (15.2 g.) is obtained.

Ethanol (152 cc.) is added to a filtered solution of this salt in distilled water (304 cc.), and then the mixture is acidified by adding N hydrochloric acid (42.5 cc.). The acid which precipitates is filtered off and washed successively with a mixture of ethanol and water (66-34 by volume), absolute ethanol and diethyl ether. After drying under reduced pressure, pure 7-(1-carboxybutoxyimino)-7H-indolizino[5,6,7-ij]isoquinoline (12.42 g.), melting at 219°C. with decomposition, is obtained.

The present invention includes within its scope pharmaceutical compositions which comprise, as active ingredient, at least one 7H-indolizino[5,6,7-ij]isoquinoline derivative of general formula I, or when appropriate a pharmaceutically-acceptable salt thereof, in association with a pharmaceutical carrier or coating. The invention includes especially such compositions made up for oral administration.

Solid compositions for oral administration include tablets, pills, powders or granules. In such solid compositions, the active compound is admixed with at least one inert diluent such as sucrose, lactose or starch. The compositions may also comprise, as is normal practice, additional substances other than inert diluents, e.g. lubricating agents such as magnesium stearate. Liquid compositions for oral administration include pharmaceutically-acceptable emulsions, solutions, suspensions, syrups and elixirs containing inert diluents commonly used in the art such as water or liquid paraffin. Besides inert diluents such compositions may also comprise adjuvants, such as wetting, emulsifying and suspending agents, and sweetening, flavouring and aromatizing agents. Compositions according to the invention for oral administration also include capsules of absorbable material such as gelatin containing the active substance with or without the addition of diluents or excipients.

The percentage of active ingredient in compositions of the invention may be varied, it being necessary that it should constitute a proportion such that a suitable dosage shall be obtained. In human therapy, the compounds of the invention are particularly suited to combat bilharzioses due to *Schistosoma mansoni, Schistosoma haematobium* and *Schistosoma japonicum*, at daily doses of between 10 and 15 mg./kg. body weight administered orally. These doses can be repeated at regular intervals of several days or several weeks in order to achieve complete elimination of the parasite.

In every case, the doctor will decide the most suitable posology, taking into account the age, weight, the degree of infestation and all other factors relating to the patient to be treated.

The following Examples illustrate pharmaceutical compositions according to the invention.

EXAMPLE 38

Tablets containing 500 mg. of active substance and having the following composition are prepared in accordance with the usual technique:

| | |
|---|---|
| 7-carboxymethoxyimino-7H-indolizino[5,6,7-ij]isoquinoline | 500 mg. |
| wheat starch | 150 mg. |
| colloidal silica | 40 mg. |
| magnesium stearate | 10 mg. |

EXAMPLE 39

Tablets containing 500 mg. of active substance and having the following composition are prepared in accordance with the usual technique:

| | |
|---|---|
| 7-ethoxycarbonylmethoxyimino-7H-indolizino-[5,6,7-ij]isoquinoline | 500 mg. |
| wheat starch | 150 mg. |
| colloidal silica | 40 mg. |
| magnesium stearate | 10 mg. |

We claim:
1. A compound of the formula:

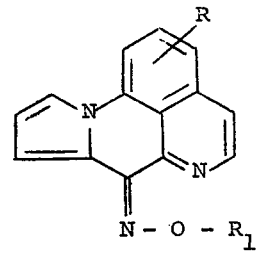

wherein R represents hydrogen, halogen, or alkoxy of 1 through 4 carbon atoms, and $R_1$ represents hydrogen, or alkyl of 1 through 4 carbon atoms mono substituted by a member of the class consisting of carboxy, alkoxycarbonyl in which the alkoxy moiety has 1 through 7 carbon atoms, and carbamoyl, or $R_1$ represents phenylalkyl in which the alkyl moiety has 1 through 4 carbon atoms and is mono substituted by a member of the class consisting of carboxy, alkoxycarbonyl in which the alkoxy moiety has 1 through 4 carbon atoms, and carbamoyl, or $R_1$ represents alkanoyl of 1 through 4 carbon atoms or benzoyl, and pharmaceutically-acceptable salts of a said compound wherein $R_1$ is substituted by carboxy.

2. A compound according to claim 1 of the formula depicted in claim 1 wherein R represents hydrogen, halogen, or alkoxy of 1 through 4 carbon atoms, and $R_1$ represents hydrogen, or alkyl of 1 through 4 carbon atoms mono substituted by a member of the class consisting of carboxy, alkoxycarbonyl in which the alkoxy moiety has 1 through 4 carbon atoms, and carbamoyl, or $R_1$ represents phenylalkyl in which the alkyl moiety has 1 through 4 carbon atoms and is mono substituted by a member of the class consisting of carboxy, alkoxycarbonyl in which the alkoxy moiety has 1 through 4 carbon atoms, and carbamoyl, or $R_1$ represents alkanoyl of 1 through 4 carbon atoms or benzoyl, and pharmaceutically-acceptable salts of a said compound wherein $R_1$ is substituted by carboxy.

3. A compound according to claim 1 of the formula:

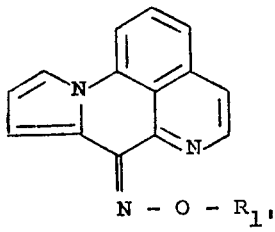

wherein $R_1$, represents alkyl of 1 through 4 carbon atoms substituted by carboxy or alkoxycarbonyl in which the alkoxy moiety has 1 through 7 carbon atoms, and pharmaceutically-acceptable salts thereof.

4. A compound according to claim 1 which is 7-carboxymethoxyimino-7H-indolizino[5,6,7-ij]isoquinoline, and its pharmaceutically-acceptable salts.

5. A compound according to claim 1 which is 7-(1-carboxyethoxyimino)-7H-iodolizino[5,6,7-ij]isoquinoline, and its pharmaceutically-acceptable salts.

6. A compound according to claim 1 which is 7-ethoxycarbonylmethoxyimino-7H-indolizino[5,6,7-ij]isoquinoline, and its pharmaceutically-acceptable salts.

7. A compound according to claim 1 which is 7-methoxycarbonylmethoxyimino-7H-indolizino[5,6,7-ij]isoquinoline, and its pharmaceutically-acceptable salts.

8. A compound according to claim 1 which is 7-(1-carboxy-propoxyimino)-7H-indolizino[5,6,7-ij]isoquinoline, and its pharmaceutically acceptable salts.

9. A compound according to claim 1 which is 7-propoxy-carbonylmethoxyimino-7H-indolizino[5,6,7-ij]isoquinoline, and its pharmaceutically acceptable salts.

10. A compound according to claim 1 which is 7-hexyloxy-carbonylmethoxyimino-7H-indolizino[5,6,7-ij]isoquinoline, and its pharmaceutically acceptable salts.

11. A compound according to claim 1 which is 7-(1-ethoxy-carbonylbutoxyimino)-7H-indolizino[5,6,7-ij]isoquinoline, and its pharmaceutically acceptable salts.

* * * * *